(12) United States Patent
Morningstar

(10) Patent No.: US 7,985,176 B1
(45) Date of Patent: Jul. 26, 2011

(54) METHOD OF IMPLANTING A PENILE PROSTHESIS

(75) Inventor: Randy L. Morningstar, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/787,847

(22) Filed: May 26, 2010

(51) Int. Cl.
*A61F 5/00* (2006.01)
(52) U.S. Cl. .......................................................... 600/40
(58) Field of Classification Search ............ 600/38–41; 128/897–899; 623/11.11, 903
See application file for complete search history.

(56) References Cited

U.S. PATENT DOCUMENTS

| | | | |
|---|---|---|---|
| 4,244,370 A * | 1/1981 | Furlow et al. | 606/148 |
| 4,350,151 A | 9/1982 | Scott | |
| 4,590,927 A | 5/1986 | Porter et al. | |
| 4,602,621 A | 7/1986 | Hakky | |
| 4,653,485 A * | 3/1987 | Fishell | 600/40 |
| 5,010,882 A | 4/1991 | Polyak et al. | |
| 5,167,611 A | 12/1992 | Cowan | |
| 5,484,450 A * | 1/1996 | Mohamed | 606/108 |
| 6,808,489 B2 | 10/2004 | George et al. | |
| 7,066,878 B2 * | 6/2006 | Eid | 600/40 |
| 7,169,103 B2 | 1/2007 | Ling et al. | |
| 7,172,602 B2 * | 2/2007 | George et al. | 606/108 |
| 2003/0220539 A1 | 11/2003 | George et al. | |
| 2004/0215056 A1 | 10/2004 | Ling et al. | |
| 2007/0175487 A1 | 8/2007 | Eid | |

FOREIGN PATENT DOCUMENTS

| | | |
|---|---|---|
| JP | 2009131310 | 6/2009 |
| WO | 0167996 A2 | 9/2001 |
| WO | 2004045421 A1 | 6/2004 |

OTHER PUBLICATIONS

1st Technical Examination for PA 2010 70210 mailed by the Danish Patent Office on Oct. 19, 2010.
International Search Report dated Oct. 28, 2010 with Written Opinion mailed on Nov. 5, 2010.
US non-final Office Action of Mar. 17, 2011.

* cited by examiner

*Primary Examiner* — Samuel G Gilbert
(74) *Attorney, Agent, or Firm* — Coloplast Corp., Coloplast A/S; Daniel G. Chapik; Nicholas R. Baumann

(57) ABSTRACT

A method of implanting a penile prosthesis into a patient includes engaging a cap that is attached to a cylinder of the penile prosthesis with a distal end of a tool, and cradling the cylinder of the penile prosthesis between two support arms of the tool. The method additionally includes inserting the two support arms of the tool and the cylinder secured between the two support arms into a corpora cavernosum of the patient.

15 Claims, 12 Drawing Sheets

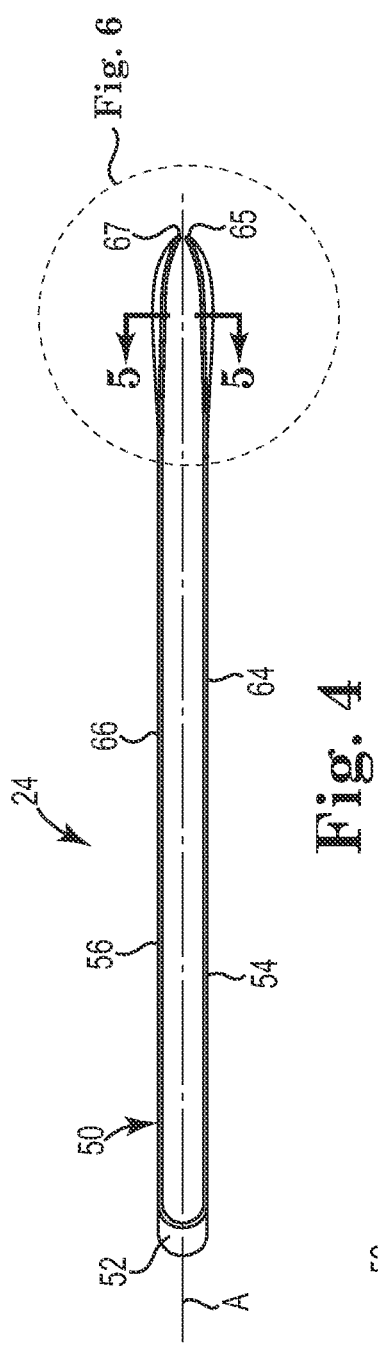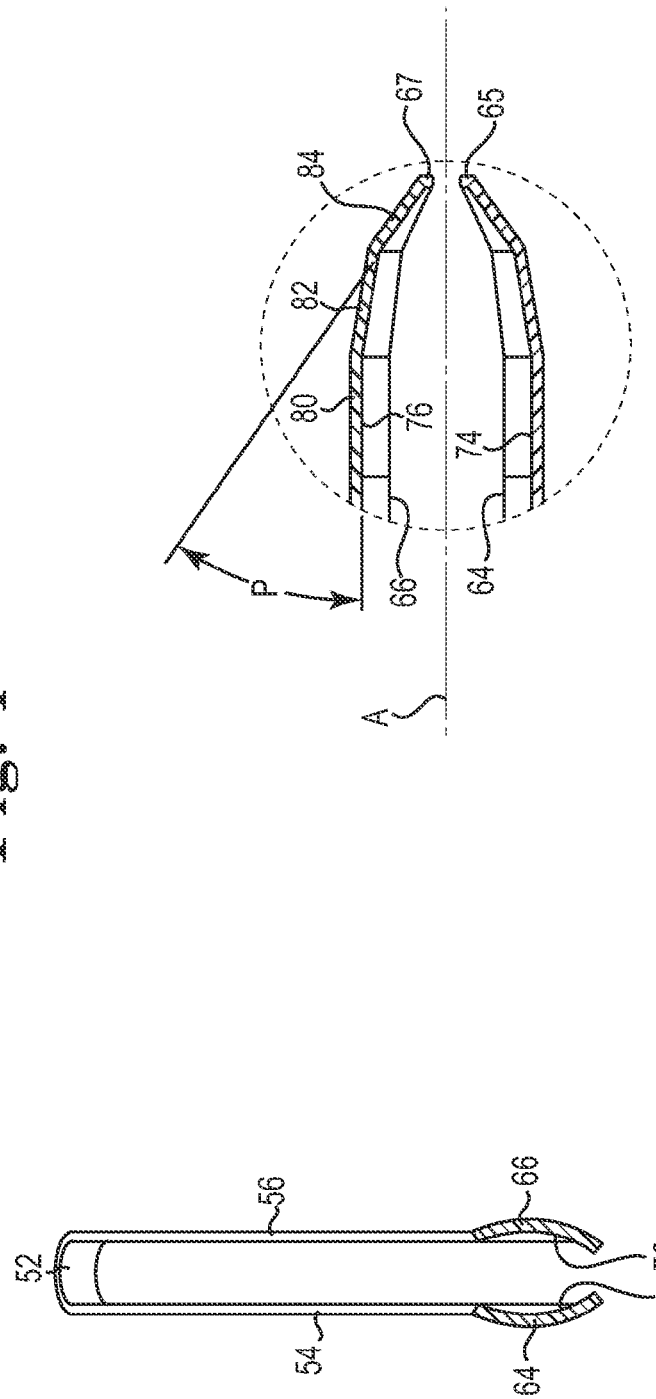

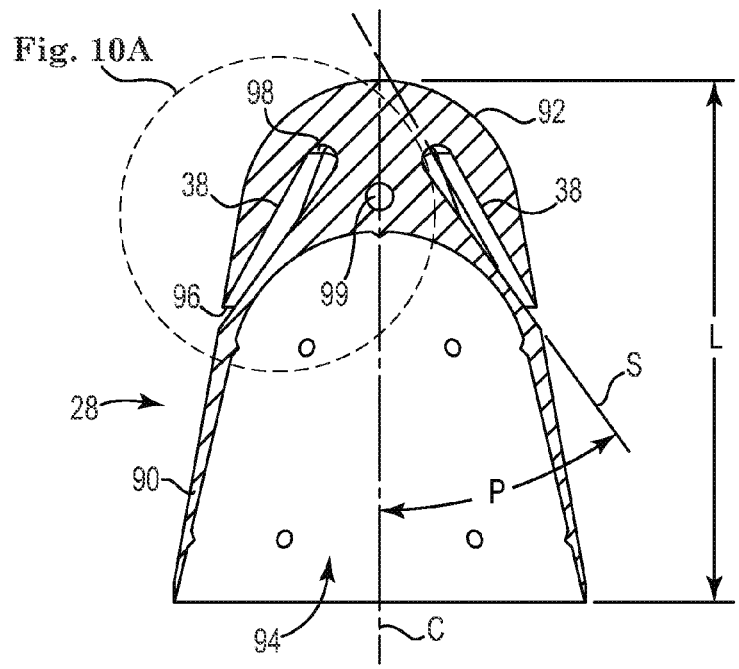
Fig. 9
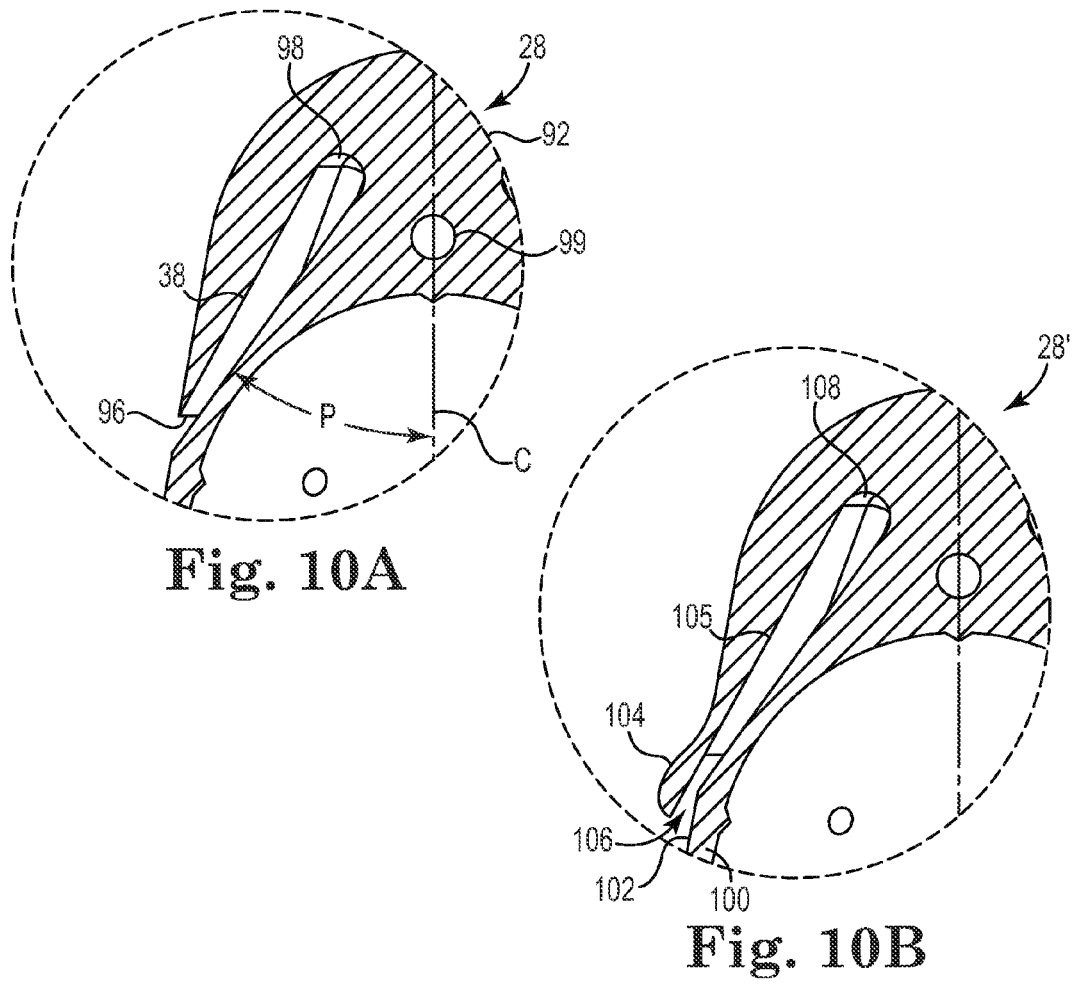
Fig. 10A
Fig. 10B

METHOD OF IMPLANTING A PENILE PROSTHESIS

BACKGROUND

Implanted penile prostheses provide relief for men with erectile dysfunction.

In a typical implantation procedure, the penis of the patient is incised to expose a pair of corpora cavernosa that are aligned axially in a side-by-side orientation within the penis. Each corpora cavernosum is dilated, for example by introducing gradually larger stainless steel rods into the corpora cavernosum until a space is created that is sized to receive a cylinder of the penile prosthesis. The cylinder is typically provided with a traction suture attached to its distal end. A tool (e.g., a "Furlow" introducer) is introduced into the space formed in the corpora cavernosum to guide a needle (e.g., a "Keith" needle) attached to the traction suture through a distal surface of the glans penis. The needle and the suture are subsequently passed through the glans penis to pull the cylinder of the penile prosthesis to a distal location within the corpora cavernosum, which locates the distal end of the prosthesis approximately mid-glans. Although the above-described approach has proven effective in treating erectile dysfunction, the needle forms a lesion in the glans penis, which can cause bleeding and discomfort to the patient.

SUMMARY

One aspect provides a cap configured to be attached to a cylinder of an implantable penile prosthesis. The cap includes a body section and a tip section. The body section defines a recess that is attachable to an end of the cylinder of the implantable penile prosthesis and the tip section terminates in a tip having a curved exterior surface. The tip section defines at least one slot formed therein that extends away from the body section and has a slot axis that intersects with a longitudinal axis of the cap.

One aspect provides a method of implanting a penile prosthesis into a patient. The method includes engaging a cap that is attached to a cylinder of the penile prosthesis with a distal end of a tool, and cradling the cylinder of the penile prosthesis between two support arms of the tool. The method additionally includes inserting the two support arms of the tool and the cylinder secured between the two support arms into a corpora cavernosum of the patient.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4 is a top view of the tool illustrated in FIG. 1.

FIG. 5 is a cross-sectional view of taken through a distal end of the tool as illustrated in FIG. 4.

FIG. 6 is an expanded top view of the distal end of the tool illustrated in FIG. 4.

FIG. 9 is a cross-sectional view of the cap illustrated in FIG. 8, where the cross-sectional view is rotated by 180 degrees relative to the orientation of FIG. 8.

FIG. 10A is an expanded cross-sectional view of a distal end of the cap illustrated in FIG. 9.

FIG. 10B is an expanded cross-sectional view of another embodiment of a cap.

DETAILED DESCRIPTION

Figure 1:
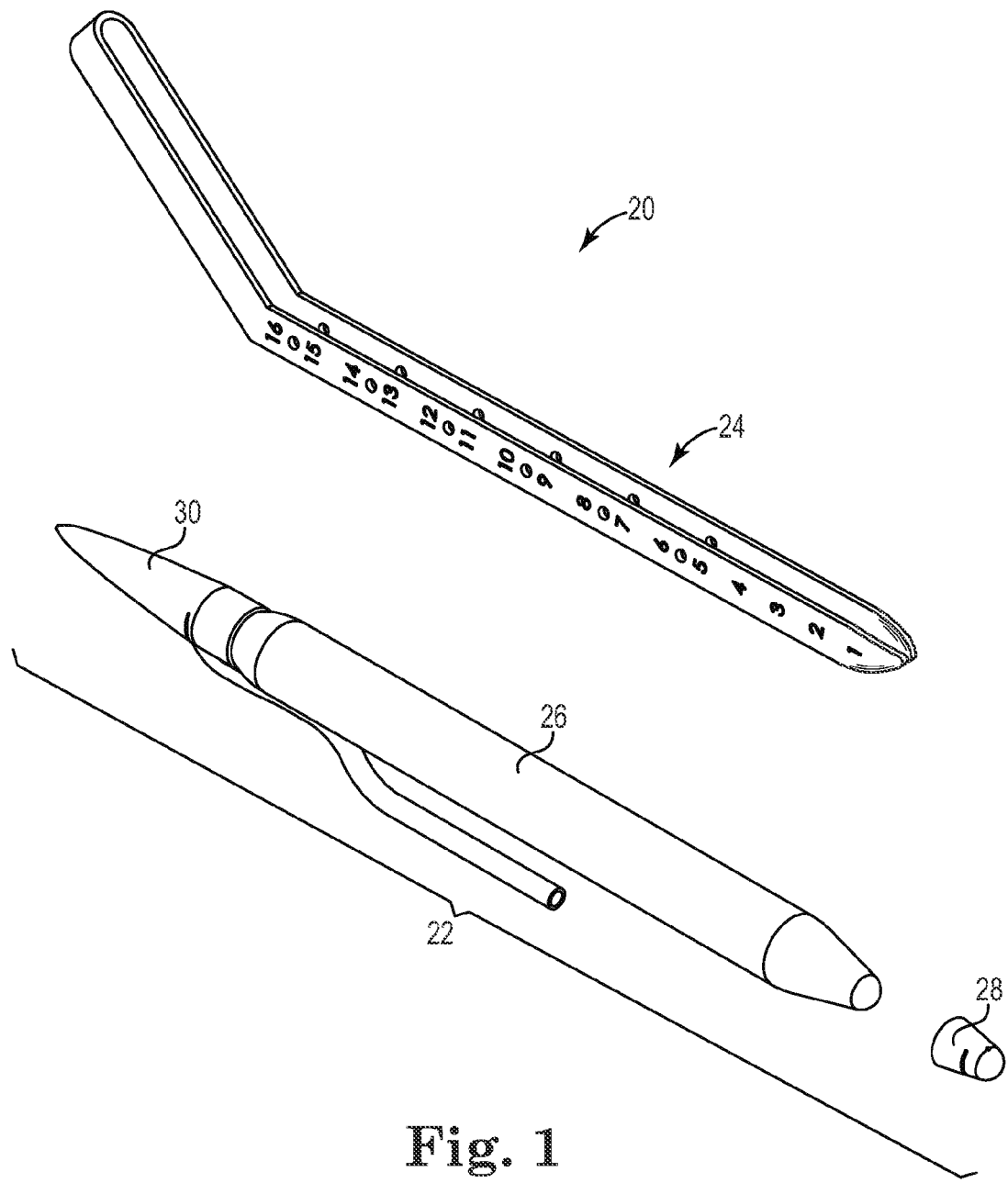
FIG. 1 is a perspective view of a system including a tool configured to implant a penile prosthesis assembly according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Soft tissue includes dermal tissue, sub-dermal tissue, ligaments, tendons, or membranes but does not include bone.

The term "proximal" as employed in this application means that part that is situated next to or near the point of attachment or origin or a central point: as located toward a center of the human body. The term "distal" as employed in this application means that part that is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis and the bulb of the penis are both located proximal relative to the male body.

An acute angle is defined to be an angle of less than 90°. At orthogonal angle is a right angle, which is an angle of 90°. Thus, an acute angle is not a right angle.

A sutureless penile prosthesis is a penile prosthesis that is characterized by an absence of a suture hole formed in a distal end of the prosthesis. Conventional penile prostheses have a suture attached to a suture hole formed in a distal end of the prosthesis, where the suture is configured to be passed through the glans penis to assist in inserting the prosthesis distally into the corpora cavernosum. In contrast, the sutureless penile prosthesis described herein has no suture hole and is configured to be inserted into a distal end of the corpora cavernosum without passing a suture or a needle through the glans penis.

Embodiments provide an implantable penile prosthesis assembly including a sutureless cylinder that is configured to be implanted into a patient. The assembly includes a cap having a tip section that defines at least one and preferably two slots that converge toward a distal end of the cap. In one embodiment, a tool is provided having converging distal end portions, where each converging distal end portion is configured to engage a respective one of the slots formed in the cap. The tool is configured to retain the prosthetic cylinder between a pair of spaced apart arms. The converging slots, in combination with the converging distal end portions of the tool, provide an engagement mechanism that enables the tool to insert the penile prosthesis cylinder into a distal end of the corpora of a penis of the patient without employing sutures.

FIG. 1 is a perspective view of a system 20 for implanting a penile prosthesis according to one embodiment. System 20 includes an implantable penile prosthesis assembly 22 and a tool 24 configured to implant assembly 22 into one of the corpora cavernosa of the patient. In one embodiment, assembly 22 includes an inflatable cylinder 26, a distal end cap 28, and a proximal end cap 30 (or rear tip extender 30). Tool 24 is configured to engage with one or both of the end caps 28, individually to facilitate implanting assembly 22 into the patient without the use of a suture as commonly employed to pull a conventional cylinder toward a distal end of the corpora cavernosum.

Figure 2:
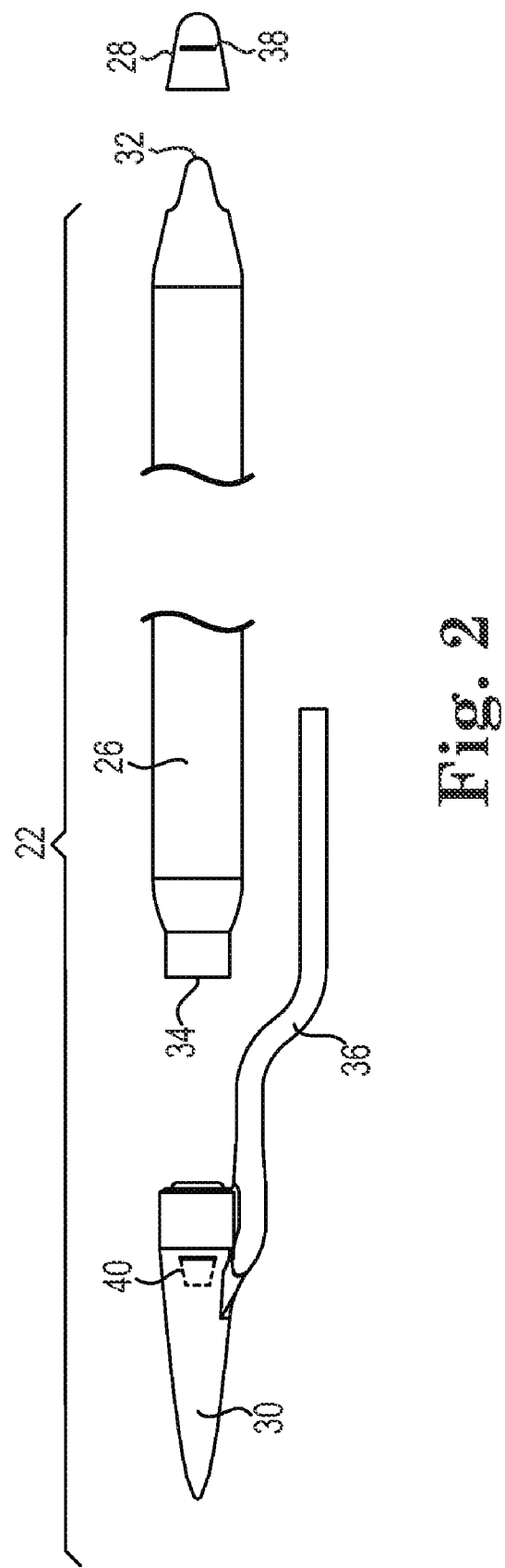
FIG. 2 is an exploded side view of the penile prosthesis assembly illustrated in FIG. 1.

FIG. 2 is an exploded side view of the penile prosthesis assembly 22. The inflatable cylinder 26 is generally provided as an oblong cylinder that is closed at distal end 32 and closed at proximal end 34 when proximal end cap 30 is attached. When so assembled, cylinder 26 is sealed and configured to be inflated when a fluid (e.g., saline typically, or a gas) is introduced into tubing 36.

In one embodiment, inflatable cylinder 26 is fabricated from a urethane material sold under the trademark Bioflex and is available from Coloplast Corp., Minneapolis, Minn. In one embodiment, distal end 32 of cylinder 26 is dipped in urethane material that cures to provide a desirable leading-end shape to cylinder 26, where the distal end 32 of cylinder 26 includes a step such that end cap 28 smoothly blends to with distal end 32 when attached to distal end 32. In one embodiment, distal end cap 28 is formed from silicone, which is dissimilar to the urethane material of the Bioflex cylinder 26. To facilitate the attachment of these two dissimilar materials, in one embodiment the urethane material of cylinder 26 is coated with fumed silica to prepare the urethane surface for bonding with the silicone cap 28.

One or both of distal end cap 28 and proximal end cap 30 are formed to include slots 38, 40, respectively, that converge inwardly into the cap and are sized to receive pincer ends of tool 24, which enables the sutureless implantation of assembly 22.

Figure 3:
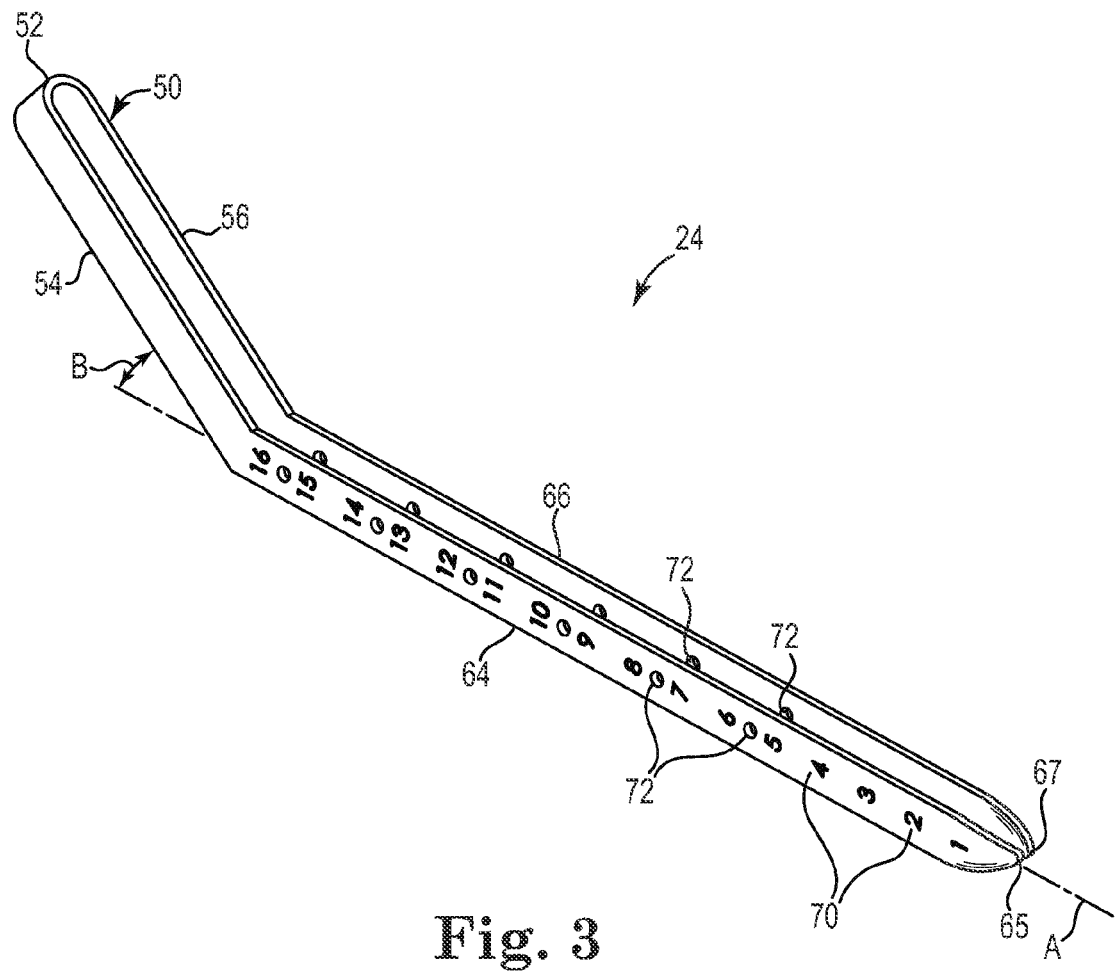
FIG. 3 is a perspective view of the tool illustrated in FIG. 1.

FIG. 3 is a perspective view of the tool 24. In one embodiment, tool 24 includes a handle 50 having a spine 52, first and second tongs 54, 56 extending from spine 52, and first and second arms 64, 66 extending from tongs 54, 56, respectively. Arms 64, 66 terminate at a pair of opposing and converging distal ends 65, 67, respectively. In one embodiment, tool 24 is formed from metal or plastic such that spine 52 provides tongs 54, 56 with a spring constant that enables arms 64, 66 to function as spring forceps. One suitable material for fabricating tool 24 includes, for example, a 22 gauge stainless steel (about 0.029 inches thick) that is electro-polished.

In one embodiment, arms 64, 66 are generally straight and extend along a major axis A of tool 24 that is disposed relative to handle 50 by an angle B. In one embodiment, angle B is in the range of 5-45° such that handled 50 is angled relative to arms 64, 66. Arms 64, 66 may be parallel or non-parallel relative to each other.

In one embodiment, at least one of the arms 64, 66 includes gradient markings 70 initiated at one of the distal ends 65, 67 and extend proximally to a location where arms 64, 66 attach to tongs 54, 56, respectively. The gradient markings 70 are configured to enable a surgeon to measure a depth of a dilated corpora cavernosum as the arms 64, 66 are inserted distally or proximally into the dilated corpora. In one embodiment, gradient markings 70 range between 0-16 cm, although other ranges for gradient markings 70 are also acceptable.

In one embodiment, each arm 64, 66 is formed to include a plurality of through-holes 72 oriented in a row. The through-holes 72 are configured to receive one or more fixation devices that are employed to immobilize the arms 64, 66 relative to a surface in the surgical field. Typically, the surgeon will attach one end of a fixation device (not shown, but see FIG. 13) to one of the through-holes 72 on one of the arms 64, 66 and another end of the fixation device to the surgical field to stabilize or otherwise hold tool 24 in place.

FIG. 4 is a top view and FIG. 5 is a cross-sectional view of tool 24. Tool 24 is configured to function as a spring forceps, in which arms 64, 66 are substantially parallel (or diverge slightly) to accommodate the placement of cylinder 26 (FIG. 2) on major axis A between arms 64, 66. Distal ends 65, 67 converge together in the form of pincers.

FIG. 5 is a cross-sectional view of tool 24 taken along line of 5-5 of FIG. 4 and illustrates one embodiment in which an inside surface 74 of a distal portion of arm 64 and an inside surface 76 of a distal portion of arm 66 are each curved to define a portion of an arc. During insertion of assembly 22 (FIG. 2), cylinder 26 is deflated to provide a "pancake-shaped" flattened cylinder. The straight, flat inside surfaces of arms 64, 66 mate against the flattened walls of cylinder 26. Cap 28 is attached to cylinder 26 and generally retains its conical shape. To this end, inside surfaces 74, 76 of arms 64, 66 curve to complement an exterior surface of cap 28 (FIG. 2), which enables the flat proximal portion of arms 64, 66 to cradle the flattened cylinder 26 and the concave inside surfaces 74, 76 of arms 64, 66 to cradle cap 28 during insertion of assembly 22 (FIG. 2).

FIG. 6 is an expanded top view of converging distal ends 65, 67 of tool 24. The major axis A of tool 24 (FIG. 3) is disposed on a centerline of tool 24 located between arms 64, 66. Generally, each distal end 65, 67 is formed to converge toward the centerline of tool 24. In one embodiment described with reference to converging distal end 67, each converging distal end portion is formed from a series of sections that gradually converge to a greater degree toward major axis A. For example, converging distal end 67 is formed from a first section 80 extending from arm 66 toward axis A, a second section 82 extending from first section 80 toward axis A, and a third section 84 extending from second section 82 toward axis A. In one embodiment, first section 80 is substantially linear relative to arm 66; second section 82 is angled by about 5-15° to converge toward major axis A; and third section 84 is angled by about 20-45° to further converge toward major axis A. In one embodiment, the series of gradually converging sections combine to deflect ends 65, 67 into pincers that have an included angle P that complements an angle of convergence for slots 38 into which ends 65, 67 are inserted.

Converging distal end 65 is likewise configured in a similar matter. Consequently, converging distal ends 65, 67 converge toward the centerline of major axis A such that ends 65, 67 are closely spaced apart, or alternatively, ends 65, 67 pinch together and touch.

In one embodiment, each section 80, 82, 84 extends for a length of between about 0.2-0.4 inches such that converging distal ends 65, 67 have a total length of between about 0.6-1.2 inches.

Figure 7:
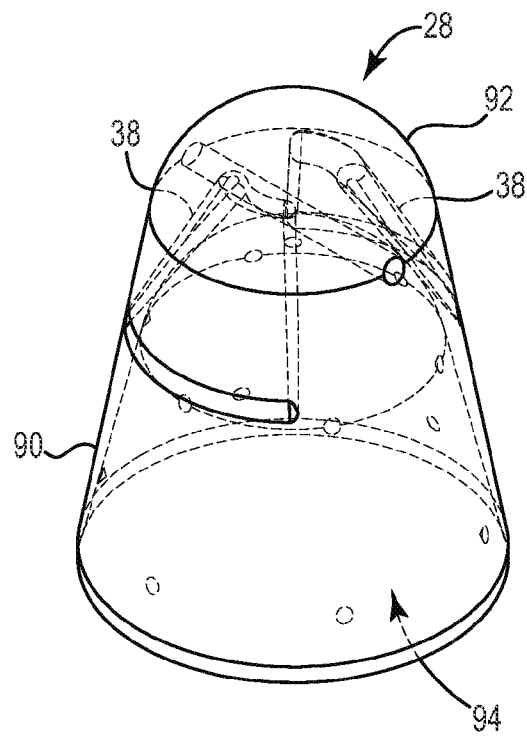
FIG. 7 is a perspective view of a cap attachable to a cylinder of a penile prosthesis according to one embodiment.
Figure 8:
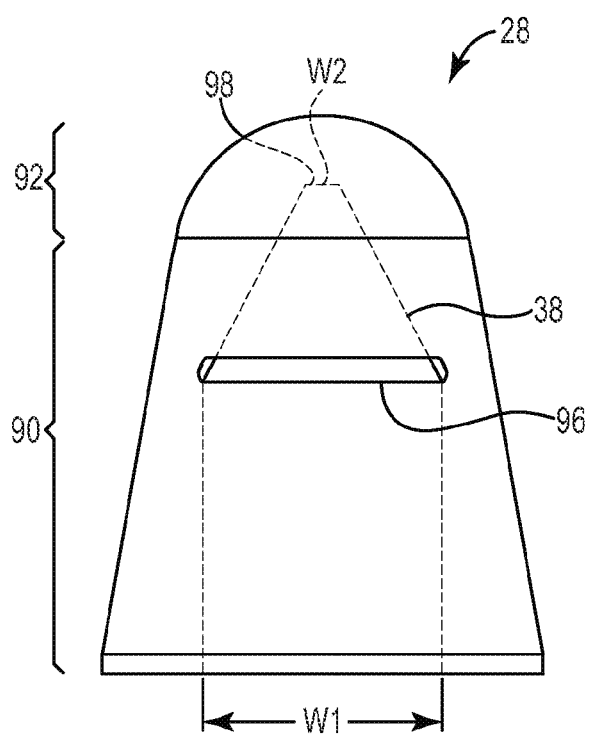
FIG. 8 is a side view of the cap illustrated in FIG. 7.

FIG. 7 is a perspective view and FIG. 8 is a side view of cap 28. In one embodiment, cap 28 includes a body section 90 and a tip of section 92, where the body section 90 defines a recess 94 that is sized to be attached over distal end 32 of cylinder 26 (FIG. 2). Body section 90 is formed as a hollow cone-shaped sleeve around recess 94 that is generally flexible and conformable to fit over distal end 32 of cylinder 26. Tip section 92 is formed or molded to be solid. In one embodiment, cap 28 is molded from silicone, although other suitable materials are also acceptable.

In one embodiment, tip section 92 provides a curved exterior surface and includes one or more slots 38 formed at least partially within tip section 92. For example, in one embodiment slot 38 extends from a slot opening 96 formed in body section 90 and terminates in a slot end 98 that is formed in tip section 92.

In another embodiment, tip section 92 provides a curved exterior surface and slots 38 extend from a slot opening 96 formed in tip section 92 and terminate in a slot end 98 also formed in tip section 92.

The slot 38 generally converges toward a center of a distal end of tip section 92 and forms a pocket that receives one of the converging ends 65, 67 of tool 24 (FIG. 4). In one embodiment best illustrated in FIG. 8, the slot opening 96 is oriented on a lateral axis as illustrated that is substantially orthogonal to the longitudinal axis C (FIG. 9), and slot 38 is formed as a tapered slot with the slot opening 96 having a lateral dimension W1 along the lateral axis that is wider than a width W2 of the slot end. Thus, slots 38 taper laterally between slot opening 96 having a width W1 and slot end 98 having a width W2, where width W1 is greater than width W2. In one embodiment, slot opening 96 extends radially about 90 degrees or more around a circumference of cap 28, such that opening 96 extends approximately 25% around the circumference of cap 28.

FIG. 9 is a cross-sectional view of cap 28. In one embodiment, cap 28 has a length L and recess 94 extends a majority of length L along a central longitudinal axis C of cap 28. The slots 38 are configured to enable the placement of cap 28 and cylinder 26 (FIG. 2) in a sutureless manner within the patient. However, some surgeons desire to have the option of placing the prosthesis distally within the penis via a suture that is employed to guide cylinder 26 distally forward within the penis. With this in mind, in one embodiment an optional suture hole 99 is formed horizontally between slots 38 and extends through tip section 92 to enable the surgeon to place the prosthesis in a manner that s/he has become accustomed to should the surgeon opt not to employ tool 24.

The central longitudinal axis C longitudinally bisects cap 28 as illustrated in FIG. 9. In one embodiment, each slot 38 extends away from body section 90 and has a slot axis S that intersects with central axis C of cap 28 in an acute angle P. In one embodiment, the angle P ranges between approximately 25-45°, with one suitable example of converging angle P being about 36°. In one embodiment, a first slot 38 is offset from a second slot 38 by 180 degrees, where each slot 38 has an axis S that intersects with the central axis C of cap 28 in an acute angle FIG. 10A is an expanded cross-sectional view of tip section 92 of cap 28. In one embodiment, slot 38 is provided with a slot opening 96 having a gap size of approximately 0.005-0.010 inches and slot end 98 is located about 0.015-0.030 inches away from opening 96 (i.e., slot 38 has a length of about 0.015-0.030 inches). Slot 38 is suitably provided as a straight slot where slot end 98 has a gap size approximately equal to the gap size of slot opening 96. Alternatively, slot end 98 has a gap size that is greater than the gap size of slot opening 96.

FIG. 10B is an expanded cross-sectional view of another embodiment of a cap 28'. Cap 28' includes a body section 100 having an outer surface 102 and a flap 104 extending from outer surface 102 to form a slot 105 extending from a slot opening 106 to a slot end 108. Ends 65, 67 of tool 24 (FIG. 3) are configured to slide under flap 104 and engage within slots 105 to facilitate implanting cap 28' and cylinder 26 (FIG. 2). In one embodiment, cap 28' is formed from silicone and flaps 104 are configured to lay flat when tool 24 is withdrawn from slots 105.

Figure 11:
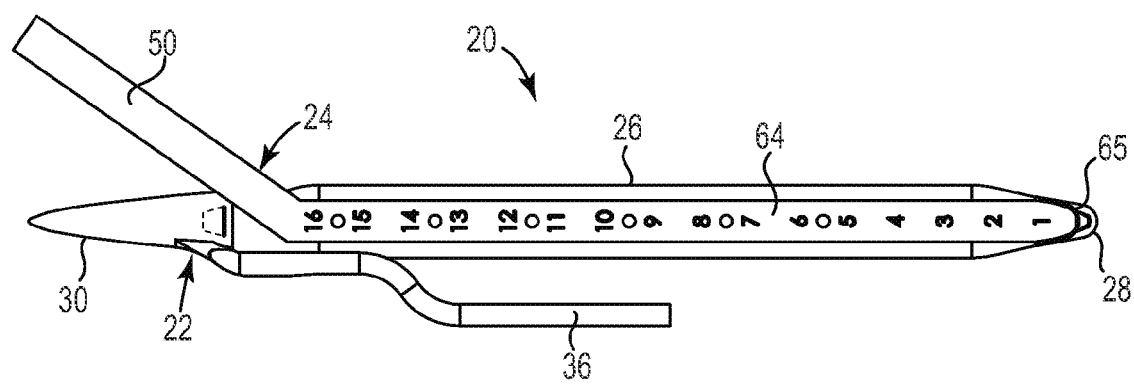
FIG. 11 is a side view of the system illustrated in FIG. 1 including the tool engaged with the penile prosthesis assembly.

FIG. 11 is a side view of system 20 including tool 24 engaged with penile prosthesis assembly 22. In preparation for the implantation procedure, a syringe or other suitable suction device is coupled to tubing 36 to evacuate and, collapse cylinder 26. Distal ends 65, 67 (one shown) of arms 64, 66 are inserted into slots 38 of cap 28. Handle 50 extends away from the major axis of cylinder 26 to provide clearance that enables improved access into a dilated corpora cavernosum of the patient, as described below.

Figure 12:
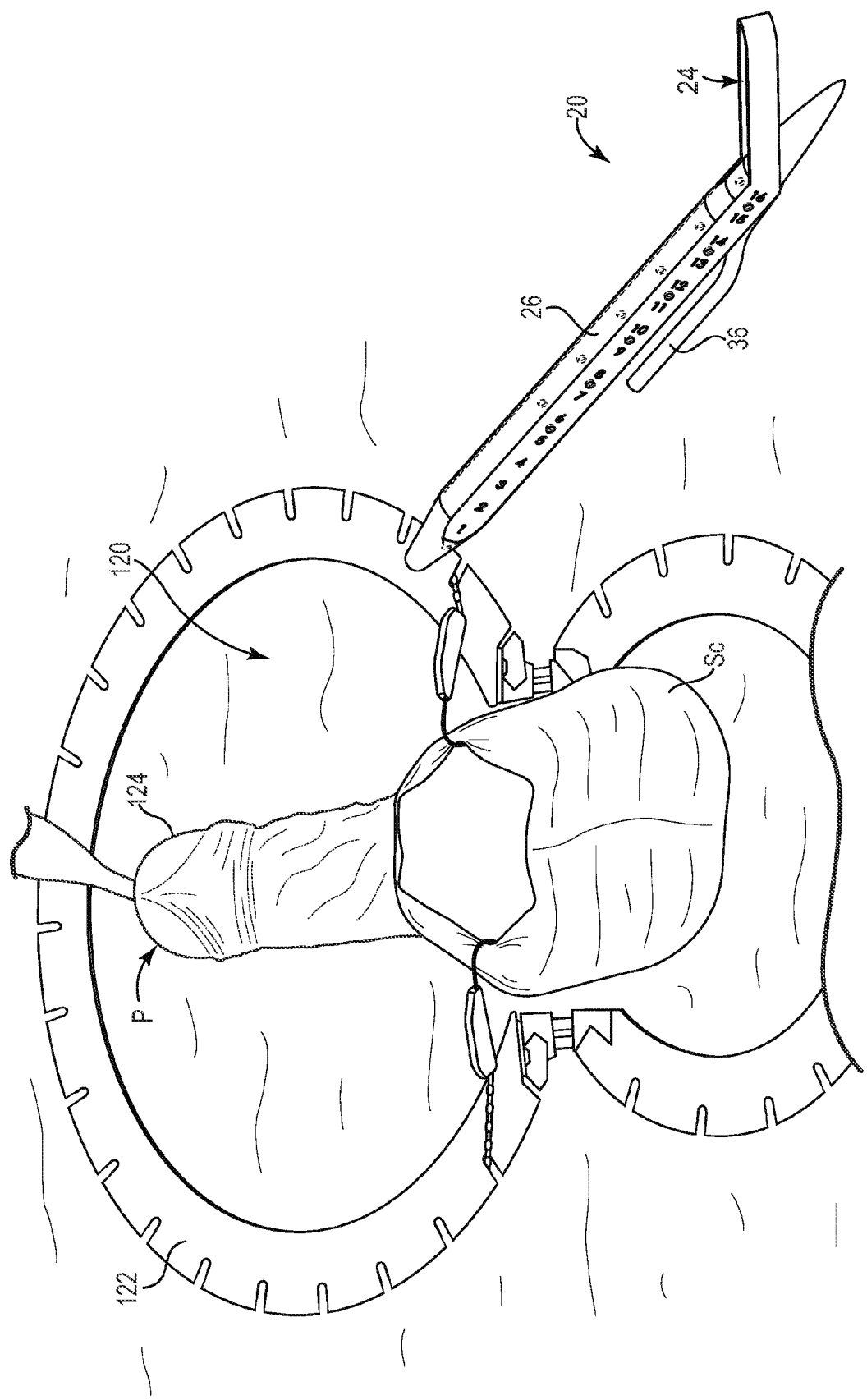
FIG. 12 is a top view of a patient prepped for the surgical implantation of the penile prosthesis assembly illustrated in FIG. 11.
Figure 13:
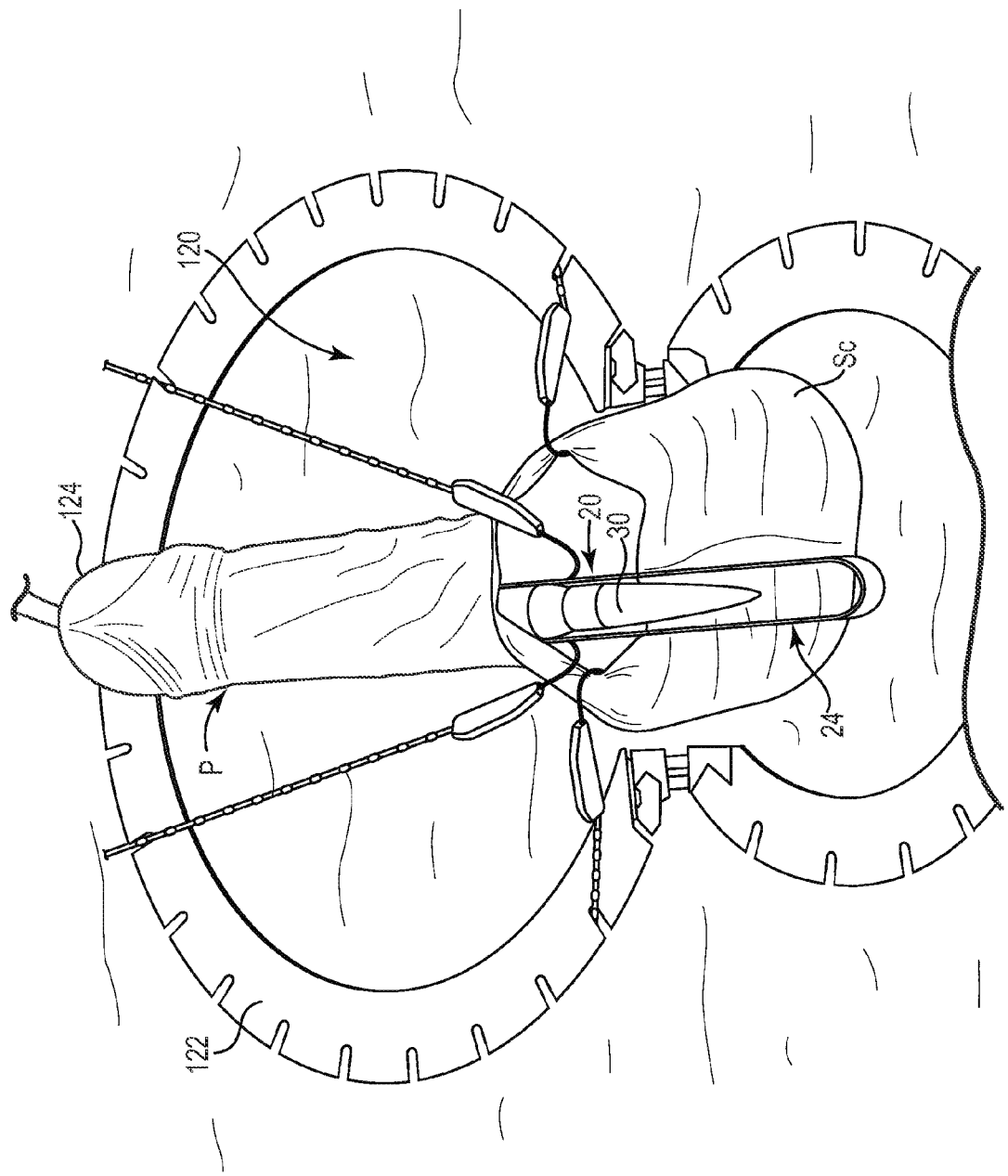
FIG. 13 is a top view of the patient with the penile prosthesis assembly inserted distally into one corpora cavernosum of the penis according to one embodiment.

FIG. 12 is a top view of the patient prepped and ready for implantation of a pair of the inflatable penile prosthesis assemblies 22 (one of which is illustrated), and FIG. 13 is a top view of the patient having one inflatable penile prosthesis assembly 22 inserted distally into one of the pair of copora cavernosa of the patient. The following description of FIGS. 12 and 13 refers to FIG. 2 (assembly 22), FIG. 3 (tool 24), and FIG. 9 (cap 28).

The groin area 120 of the patient is cleaned, shaved, and suitably prepped with, for example, a surgical solution prior to draping with a sterile drape. A retraction device, such as a retractor 122 sold under the trademark Lone Star and available from Lone Star Medical Products of Stafford, Tex., is placed around the penis P. Thereafter, the surgeon forms an incision to access the corpora covernosum of the patient, where suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc. As an example of the transverse scrotal approach, the surgeon forms a 2-3 cm transverse incision through the subcutaneous tissue of the median raphe of the upper scrotum Sc and dissects down through the Dartos fascia and Buck's fascia to expose the tunicae albuginea of the penis P. Thereafter, each corpora cavernosum is exposed in a corporotomy where a small (approximately 1.5 cm) incision is formed to enable the surgeon to access and dilate the corpora cavernosum. The corpora cavernosum is dilated distally and proximally with a suitable expanding tool to create a space for cylinder 26. For example, the surgeon begins dilation of both the distal and proximal corpora cavernosum by introducing an 8 mm dilator into the spongy tissue of the corpora with sequential progression to about a 14 mm dilator, each of which are introduced and pushed distally toward the glans penis and the crus of the penis, respectively. In one embodiment, after dilation of the corpora cavernosum, the surgeon employees the gradient markings 70 of tool 24 to measure a length of the dilated corpora cavernosum, which facilitates selection of the proper length of assembly 22 (e.g., cylinder 26 and ends 28, 30) for implantation. In one embodiment, the surgeon employees tool 24 to at least partially (or further) dilate the corpora cavernosum.

After dilation of a first of the corpora cavernosa, the primed and deflated sutureless cylinder 26 is inserted through the corporotomy with tool 24. As regards distal placement, for example, the cap 28 is introduced into the dilated corpora cavernosum through the corporotomy and the surgeon employs handle 50 to push the ends 65, 67 of insertion tool 24 distally to direct cylinder 26 to the distal-most portion of the corpora cavernosum. The surgeon may palpate the end of penis P at the subcoronal area 124 to locate the distal end of cap 28 to ensure proper placement of penile prosthesis assembly 22 interior to a corona of glans penis of the patient. Notably, the sutureless cylinder 26 is thus located in the distal-most and portion of the corpora cavernosa without the use of a suture threaded through the glans penis.

The proximal end 30 of the penile prosthesis assembly 22 is implanted into the proximal corpora cavernosum, which is typically completed after implantation of the distal end of assembly 22 (the order of implantation is based on surgeon preference). To facilitate placement of the proximal end 30 of the sutureless penile prosthesis assembly 22, tool 24 is provided with apertures 72 formed in arms 64, 66 (FIG. 3) that enable the surgeon to stabilize the inserted tool 24 relative to retractor 122. For example, a tie-down or other fixation device is attached between aperture 72 and retractor 122 as illustrated in FIG. 13 such that tool 24 and the distal end of assembly 22 is held in place within the distal end of the corpora cavernosum, which maintains the proper insertion orientation of cylinder 26 within the distal corpora cavernosum. The stabilization of the distal end of assembly 22 is useful in properly placing the proximal end 30 of penile prosthesis assembly 22 into the proximal corpora cavernosa.

Figure 14A:
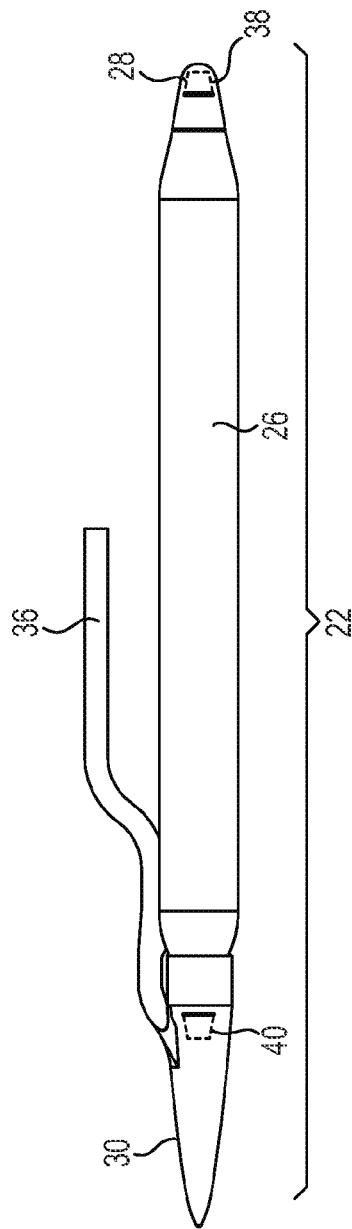
FIG. 14A is a side view of the penile prosthesis assembly including a proximal rear tip cap having a slot sized to receive the tool illustrated in FIG. 3.
Figure 14B:
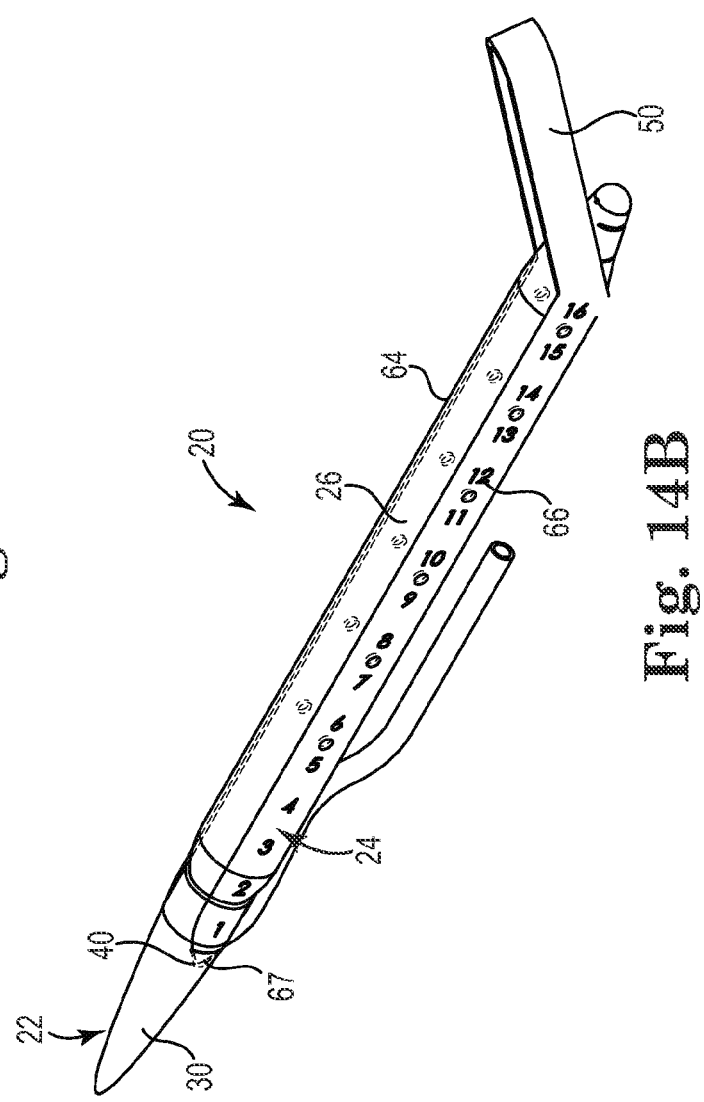
FIG. 14B is a perspective view of the tool illustrated in FIG. 3 attached to the rear tip cap of the penile prosthesis assembly illustrated in FIG. 14A.

FIG. 14A is a side view of penile prosthesis assembly 22 including proximal end 30 provided with slot 40. Proximal end cap 30 includes a recess that is attachable to the proximal end 34 of cylinder 26 and is configured for implantation proximally toward a crus of the penis P. FIG. 14B is a perspective view of a separate or second tool 24 engaged with slot 40 and readied for insertion of proximal end tip 30 into the proximal corpora cavernosum (the proximal corpora cavernosum is dilated with dilation introducers in a manner similar to the dilation of the distal corpora cavernosa as described above). In one embodiment, distal ends 65, 67 are each engaged with one of the slots 40 such that arms 64, 66 cradle cylinder 26 and handle is available to direct the proximal end tip 30 into the proximal corpora cavernosum toward a crus of the penis P.

After insertion of proximal end tip 30 into the proximal corpora cavernosum, tool 24 is removed from assembly 22 leaving proximal end tip inserted in the proximal corpora cavernosum. Thereafter, the fixation devices are removed from between apertures 72 and retractor 122 and tool 24 is removed from cap 28 leaving cylinder 26 inserted into the distal corpora cavernosum. The corporotomy is closed, and the remaining portions, for example a reservoir and/or a pump, are implanted in the abdomen and scrotum Sc, respectively, of the patient.

Figure 14C:
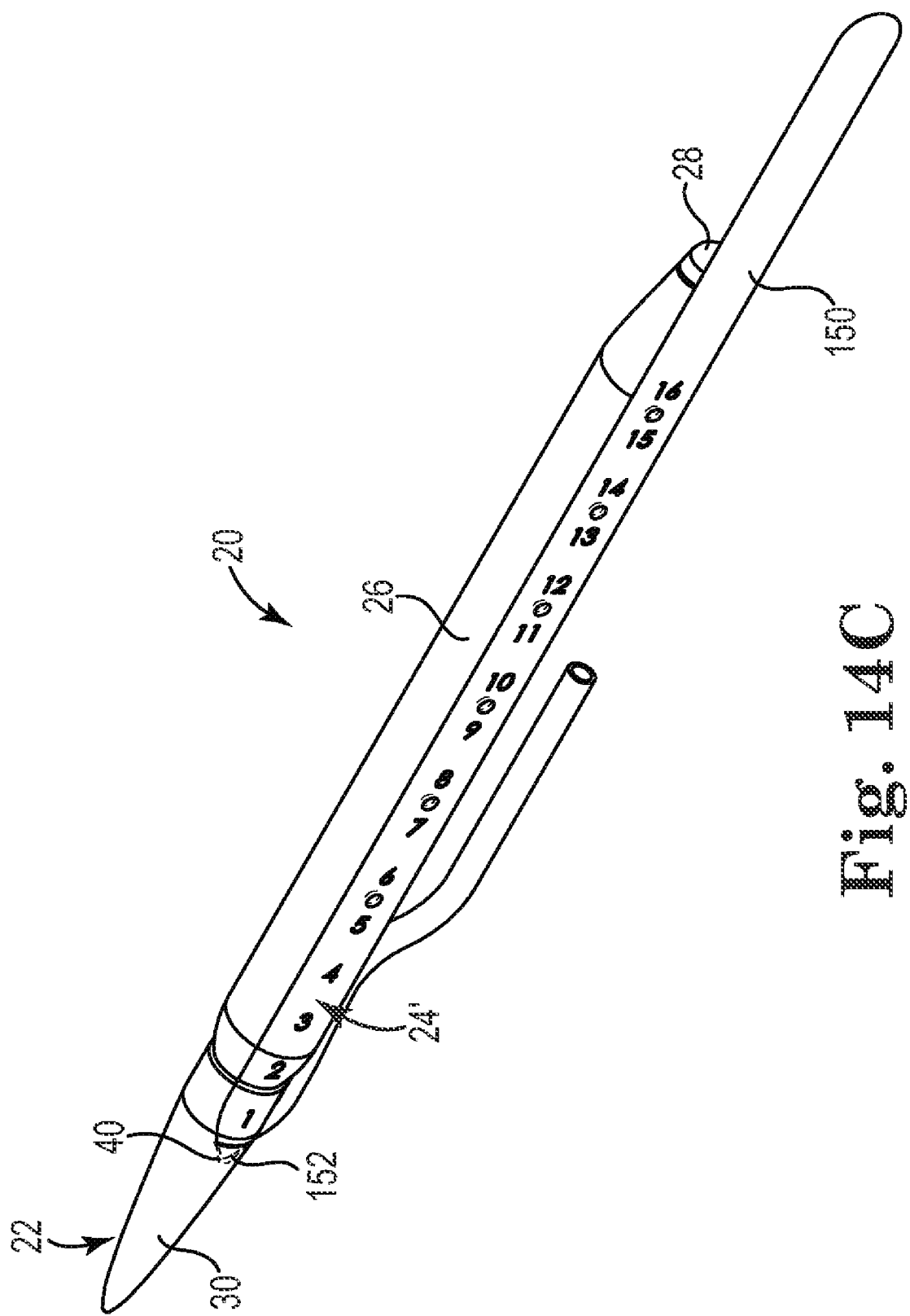
FIG. 14C is a perspective view of the penile prosthesis assembly illustrated in FIG. 1 and another embodiment of a tool configured to implant assembly into one of the corpora cavernosa of the patient.

FIG. 14C is a perspective view of implantable penile prosthesis assembly 22 and another embodiment of a tool 24' configured to implant assembly 22 into one of the corpora cavernosa of the patient. The inflatable cylinder 26, distal end cap 28, and proximal end cap 30 (or rear tip extender 30) are each substantially as described above. In one embodiment, tool 24' is provided as a single linear arm implement that is configured to engage with one or both of the end caps 28, 30 individually to facilitate implanting assembly 22 into the patient without the use of a suture as commonly employed to pull a conventional cylinder toward a distal end of the corpora cavernosum. Tool 24' includes one linear arm 150 having a distal end 152 that is curved or angled out of the plane of arm 150. To this end, distal end 152 of arm 150 is configured to engage with slot 38 of distal tip 28 or slot 40 of proximal tip to gain traction for insertion of the implant. In particular, the angled or converging nature of slots 38, 40 provide tool 24' with traction for insertion of assembly 22. In addition, the linear conformation of tool 24' is configured to provide low friction removal of tool 24' after implantation of assembly 22.

Figure 15:
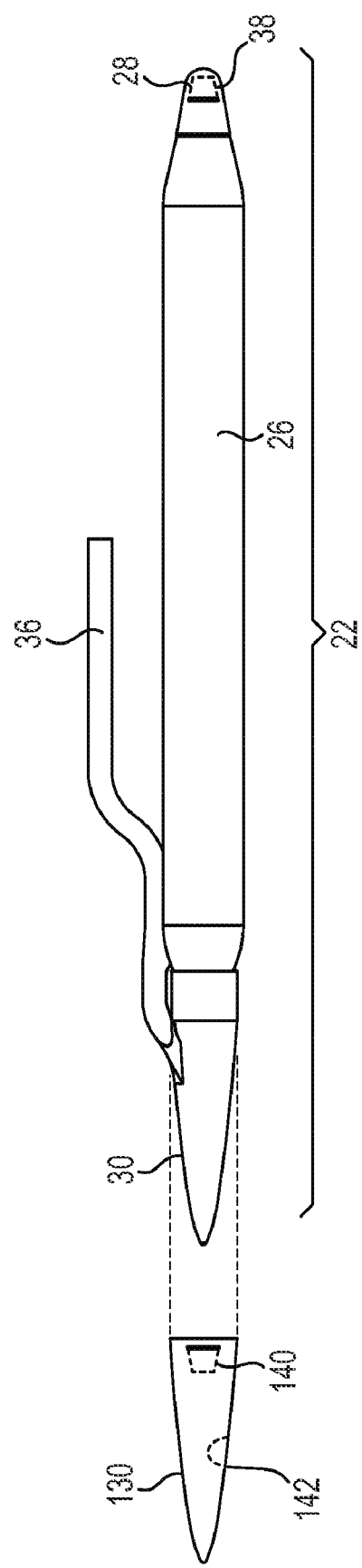
FIG. 15 is a side view of a rear tip extender attachable to the penile prosthesis assembly illustrated in FIG. 2 according to one embodiment.

FIG. 15 is a side view of a rear tip extender 130 attachable to penile prosthesis assembly 22 according to one embodiment. Rear tip extenders are sometimes attached to assembly 22 to increase the length of the assembly. Slot 40 formed in proximal end cap 30 is still available to receive tool 24 even after rear tip extender 130 is attached to assembly 22. However, in this optional embodiment rear tip extender 130 is attachable to proximal end 30 of assembly 22 and includes at least one slot 140 that is also configured to receive tool 24. Slot 140 is similar to slot 38 (FIG. 9) or slot 40 (FIGS. 2 and 14A) and is configured to engage with distal ends 65, 67 (FIG. 3) of tool 24 to enable tool 24 to insert proximal end of assembly 22 into a proximal corpora cavernosum of the patient. For example, in one embodiment rear tip extender 130 is a cap having a recess 142 formed in its body section and is sized to be attachable to proximal end 30 of cylinder 26 for implantation proximally toward a crus of the penis P (FIG. 12). Depending upon the size of the patient, and upon surgeon preference, the procedure may indicate that the selected size of assembly 22 is less than entirely optimal. In such a case, the surgeon may desire to add length to assembly 22 by attaching rear tip extender 130 to proximal end 30 of cylinder 26. Slot 140 in rear tip extender 130 enables the sutureless insertion of assembly 22/extender 130 in a manner similar to that described above in reference to FIGS. 14A and 14B.

Embodiments of a cap attachable to an implantable penile prosthesis, an assembly, and a system for implanting such an assembly have been described. The cap provides converging slots that engage with converging distal ends of the tool to provide an engagement mechanism that enables insertion of penile prostheses into corpora of a penis without employing guide sutures in the glans penis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A method of implanting a penile prosthesis into a patient, the method comprising:
   engaging a cap that is attached to a cylinder of the penile prosthesis with a distal end of a tool;
   cradling the cylinder of the penile prosthesis between two support arms of the tool; and
   inserting the two support arms of the tool and the cylinder secured between the two support arms into a corpora cavernosum of the patient.

2. The method of claim 1, comprising engaging a cap that is attached to a sutureless penile prosthesis with a distal end of a tool.

3. The method of claim 1, wherein engaging a cap that is attached to a cylinder of the penile prosthesis with a distal end of a tool comprises sliding each one of a pair of converging distal ends of a tool into a respective slot formed in an opposing side of the cap, each slot angled to converge toward an end of the cap.

4. The method of claim 3, comprising guiding the end of the cap interior a corona of glans penis of the patient with the tool.

5. The method of claim 3, comprising guiding the end of the cap toward a crus of a penis of the patient with the tool.

6. The method of claim 1, comprising engaging a cap that is attached to a distal end of a cylinder of the penile prosthesis with a distal end of a tool and inserting the two support arms of the tool and the cylinder secured between the two support arms into a corpora cavernosum of the patient and toward a glans penis of the patient; and
   engaging a cap that is attached to a proximal end of a cylinder of the penile prosthesis with a distal end of a tool and inserting the two support arms of the tool and the cylinder secured between the two support arms into a proximal portion of the corpora cavernosum that extends adjacent a crus of penis of the patient.

7. The method of claim 1, comprising securing the support arms of the tool to a retractor.

8. The method of claim 7, comprising detaching the support arms of the tool from the retractor and removing the tool from the corpora cavernosum of the patient.

9. The method of claim 1, wherein at least one of the two support arms of the tool comprises a length marking, and further comprising:
   measuring a length of the corpora cavernosum of the patient with the length marking of the tool; and
   selecting a length of the cylinder of the penile prosthesis according to the measured length of the corpora cavernosum.

10. The method of claim 1, further comprising:
    at least partially dilating the corpora cavernosum with the tool.

11. A method of implanting a penile prosthesis into a patient, the method comprising:
    accessing a corpora cavernosum of the patient;
    dilating the corpora cavernosum of the patient;
    securing a cylinder of a sutureless penile prosthesis between two support arms of a tool; and
    inserting the sutureless penile prosthesis into the dilated corpora cavernosum of the patient with the two support arms of the tool.

12. The method of claim 11, comprising engaging two converging distal ends of the tool with respective slots formed in a cap attached to the sutureless penile prosthesis.

13. The method of claim 12, comprising engaging the two converging distal ends of the tool with respective slots formed in a cap attached to a proximal end of the sutureless penile prosthesis.

14. The method of claim 11, further comprising:
    measuring a length of the dilated corpora cavernosum of the patient with indicia marked on at least one of the two support arms of the tool.

15. The method of claim 11, further comprising:
    securing a fixation line between an aperture formed in each of the two support arms of the tool and a retraction device placed on the patient.

\* \* \* \* \*